United States Patent
Sadano et al.

(10) Patent No.: US 7,112,689 B2
(45) Date of Patent: Sep. 26, 2006

(54) METHOD FOR THE PRODUCTION OF A LUTEIN-FATTY ACID ESTER CONCENTRATE

(75) Inventors: Shin Sadano, Kameoka (JP); Koichi Harada, Kameoka (JP); Tadamichi Sonoda, Tokyo (JP)

(73) Assignee: Riken Vitamin Co., Ltd., Tokyo (JP)

( * ) Notice: Subject to any disclaimer, the term of this patent is extended or adjusted under 35 U.S.C. 154(b) by 764 days.

(21) Appl. No.: 10/331,615

(22) Filed: Dec. 31, 2002

(65) Prior Publication Data

US 2003/0130531 A1 Jul. 10, 2003

(30) Foreign Application Priority Data

Jan. 8, 2002 (JP) ............................. 2002-001824

(51) Int. Cl.
*C07B 51/43* (2006.01)
(52) U.S. Cl. ..................................... 554/206
(58) Field of Classification Search ................ 554/548, 554/532, 533, 546, 514, 206
See application file for complete search history.

(56) References Cited

U.S. PATENT DOCUMENTS 4,048,203 A 9/1977 Philip
6,191,293 B1 2/2001 Levy

FOREIGN PATENT DOCUMENTS

WO 97/23436 7/1997
WO 98/45241 * 10/1998

OTHER PUBLICATIONS

J. K. Tycskowski et al., " Research Notes: Preparation of Purified Lutein and its Diesters from Extracts of Marigold (Tagetes erecta)", Poultry Science, vol. 70, No. 3, pp. 651-654, 1991.
Database WPI, Section Ch, Week 200235, Derwent Publications Ltd., London, GB; AN 2002-311245 XP0022522730 & JP 2002-030068 A, Jan. 29, 2002 * abstract *.
T. Phillip et al., "A Process for the Purification of Lutein-Fatty Acid Esters from Marigold Petals", Journal of Food Science, vol. 41, No. 1, pp. 163-164, 1976.
Ai-Wu Sheng et al., "Preliminary Studies on the Extraction Methods and Characteristics of Marigold Pigments", Journal of Zhongkai Agritechnical College, vol. 14, No. 4, pp. 38-41, 2001 with English abstract.

* cited by examiner

*Primary Examiner*—Deborah D. Carr
(74) *Attorney, Agent, or Firm*—Wenderoth, Lind & Ponack, L.L.P.

(57) ABSTRACT

The present invention relates to a method for the production of a lutein-fatty acid ester concentrate of high purity by dissolving marigold oleoresin in a ketone solvent such as acetone, cooling the solution, and removing wherefrom a ketone solvent-insoluble component to uniform the quality of oleoresin, followed by dissolving the acetone-soluble portion obtained as above in butanol, cooling the solution, removing a butanol-soluble impurity after adding or without adding one or more members selected from the group consisting of water, methanol, ethanol and a mixture thereof, and washing the resulting butanol-insoluble with ethanol.

10 Claims, No Drawings

METHOD FOR THE PRODUCTION OF A LUTEIN-FATTY ACID ESTER CONCENTRATE

BACKGROUND OF THE INVENTION

1. Field of the Invention

The present invention relates to a method for the production of a lutein-fatty acid ester concentrate, more particularly a method of obtaining a lutein-fatty acid ester concentrate of high purity by purifying marigold oleoresin.

2. Description of the Prior Art

Lutein-fatty acid esters are a yellow-orange pigment contained in fruits such as oranges, peaches, papayas, prunes and mangos. Lutein-fatty acid esters are also present in many flowers and vegetables, particularly in petals of marigold flowers remarkably. Dried and ground marigold flowers have been used as animal feeds for a long time, and oleoresin which is obtained by extraction of marigold flowers with a solvent has also been widely used as food color in recent years in addition to the above-mentioned application.

The recent scientific researches have reported that lutein is associated with risk reduction for age-related macular degeneration (AMD) caused by oxidative damage to macular area of retina (Journal of the American Medical. Association, 272, 1413–1420, 1994: Investigative Ophthalmology & Visual Science, 38, 1802–1811, 1997, etc.), and that lutein is effective for prevention of arteriosclerosis, prevention of cataract or suppression of carcinogenesis and etc. (British Medical Journal, 305, 335–339, 1992: The American Journal of Clinical Nutrition, 70, 517–524, 1992: American Journal of Epidemiology, 149, 801–809, 1999, etc). As such the use of lutein as a health food and a dietary supplement is also expected.

Marigold oleoresin is obtained when dried and ground marigold flowers are extracted with a hydrocarbon solvent such as hexane and petroleum ether or with a chlorinated hydrocarbon solvent such as dichloromethane, and the solvent is removed from the extract. But the content of lutein-fatty acid ester as an ester contained in oleoresins produced by the largest producers of marigold extracts is low, usually 14 to 20% (cf. U.S. Pat. No. 6,191,293), and is about 30 to 35% even in a superior grade type which is partly sold for food.

Thus, there has been a demand for a lutein-fatty acid ester concentrate of high purity in order to obtain more vivid color tones when it is used as a food color and in order to improve the functional efficiency when it is used as a dietary supplement.

As to a method of obtaining a lutein-fatty acid ester concentrate of high purity, "Purification of Lutein-Fatty Acid Esters From Plant Materials" (U.S. Pat. No. 4,048,203) and "Trans-xanthophyll Ester Concentrates of Enhanced Purity and Methods of Making Same" (U.S. Pat. No. 6,191, 293) have been disclosed.

The former describes a method which comprises precipitating lutein-fatty acid esters from oleoresin which is dissolved in hot alkanol containing not more than four carbon atoms by cooling the solution, removing alkanol wherefrom by filtration and drying the lutein-fatty acid ester under vacuum. However, the purity of the lutein-fatty acid ester concentrate obtained by this method is 51%, which cannot be considered a high purity.

The latter describes a method of obtaining a purified trans-xanthophyll ester by contacting coronals (or flowers) of marigold flowers with a hydrocarbon solvent, removing wherefrom plant residue after sufficient extraction, evaporating the extract to obtain oleoresin, admixing the resulting oleoresin with an alcohol at ambient temperature and removing the alcohol containing impurity and cis-xanthophyll ester from the mixture.

By this method, however, the purity of lutein-fatty acid ester in the resulting oleoresin varies widely depending on the quality of the raw material, i.e. coronals (or flowers) of marigold flowers, and therefore, the purity of lutein-fatty acid ester in a concentrate obtained by purifying the said oleoresin also varies widely. For this reason, control of the raw material is necessary to obtain a lutein-fatty acid ester concentrate of high purity by this method, and as such it is difficult to stably obtain a lutein-fatty acid ester concentrate of high purity when most of the commercially available oleoresins are used as a starting material.

SUMMARY OF THE INVENTION

An object of the present invention is to provide a production method by which a lutein-fatty acid ester concentrate of high purity can be stably obtained even when oleoresin containing lutein-fatty acid esters of low purity is used as a starting material, without being affected by variation of the quality, particularly the content of lutein-fatty acid esters, of marigold oleoresin.

The present inventors have found that, as a result of diligent studies to solve the above-mentioned problems, a lutein-fatty acid ester concentrate of high purity is stably obtained by dissolving oleoresins in a ketone solvent such as acetone, cooling the solution, and removing wherefrom an insoluble component in a ketone solvent such as phospholipid to uniform the quality of oleoresins, dissolving a ketone solvent-soluble portion obtained as above in butanol, cooling the solution, removing a butanol-soluble impurity after adding or without adding one or more members selected from the group consisting of water, methanol and ethanol to the solution, and washing the resulting butanol-insoluble with ethanol. The present inventors have accomplished the present invention after further studies based on the finding.

Thus, the present invention is directed to the following (1) to (9).

(1) A method for the production of a lutein-fatty acid ester concentrate of high purity from marigold oleoresin, which comprises:

(a) a step of dissolving marigold oleoresin in a ketone solvent, cooling the solution and removing wherefrom a ketone solvent-insoluble impurity, (b) a step of dissolving a ketone solvent-soluble portion, obtained by removing a ketone solvent from the ketone solvent solution, in butanol, cooling the solution and eliminating a butanol-soluble impurity, and (c) a step of washing a butanol-insoluble, which is obtained after the above cooling process, with ethanol to eliminate an ethanol-soluble impurity, followed by removing a residual solvent to obtain a lutein-fatty acid ester concentrate of high purity.

(2) A method for the production of a lutein-fatty acid ester concentrate of high purity from marigold oleoresin, which comprises:

(a) a step of dissolving marigold oleoresin in a ketone solvent, cooling the solution and removing wherefrom a ketone solvent-insoluble impurity, (b) a step of dissolving a ketone solvent-soluble portion, which is obtained by removing a ketone solvent from the ketone solvent solution, in butanol, cooling the solution, adding thereto one or more solvents selected from the group consisting of water, methanol, ethanol and a mixture thereof, and then eliminating a butanol-soluble impurity, and (c) a step of washing a butanol-insoluble, which is obtained upon addition of the said solvent (s) after cooling, with ethanol to eliminate an ethanol-soluble impurity, followed by removing a residual solvent to obtain a lutein-fatty acid ester concentrate of high purity.

(3) A method for the production of a lutein-fatty acid ester concentrate of high purity, which comprises dissolving marigold oleoresin in a ketone solvent, cooling the solution and removing wherefrom a ketone solvent-insoluble impurity.

(4) The method for the production of a lutein-fatty acid ester concentrate of high purity according to any one of the above (1) to (3), wherein the ketone solvent is acetone.

(5) A method for the production of a lutein-fatty acid ester concentrate of high purity, which comprises washing a butanol-insoluble, which is precipitated from a butanol solution containing lutein-fatty acid ester obtained by processing marigold oleoresin, with ethanol.

(6) The method for the production of a lutein-fatty acid ester concentrate of high purity according to any one of the above (1) to (5), wherein butanol is n-butanol.

(7) A composition comprising not less than 70 wt % of lutein-fatty acid esters.

(8) A health food or a dietary supplement comprising not less than 70 wt % of lutein-fatty acid esters.

(9) A method of making a health food or a dietary supplement which comprises incorporating a composition containing not less than 70 wt % of lutein-fatty acid esters into a health food or a dietary supplement.

DETAILED DESCRIPTION OF THE INVENTION

Marigold oleoresin used in the present invention is a solid or a viscous liquid having yellow-orange/yellowish-brown color, which is obtained by drying flowers of marigold which is a member of the Compositae family (Tagetes erecta WILLD.), grinding the dried product, optionally converting into pellet, extracting with an organic solvent, usually hexane, and removing the solvent from the extract. Its main component is lutein (one of xanthophylls) dipalmitate.

According to the method of the present invention, marigold oleoresin (also called oleoresin for short) is dissolved in a ketone solvent. A ketone solvent used here includes a ketone solvent containing 3 to 9 carbon atoms such as acetone, methylethylketone and diethylketone, among which acetone is preferable. The amount of acetone is about 0.5 to 10 parts by weight, preferably about 2 to 3 parts by weight, relative to 1 part by weight of marigold oleoresin which is the raw material.

A mixture of oleoresin and acetone is stirred for about 0.5 to 1 hour at about 40 to 55° C., preferably at about 45 to 50° C. while keeping moderate refluxing. Next the mixture is slowly cooled to about 10 to 30° C., preferably about 15 to 25° C. over a period of usually about 2 to 4 hours. The cooled mixture is filtered through filter paper or filter fabric with filter aid, if necessary, such as diatomite. The filtrate is evaporated under reduced pressure and acetone is removed wherefrom to obtain a solid or a viscous liquid consisting of acetone-soluble portion in oleoresin.

According to the method of the present invention, acetone-soluble portion in oleoresin is dissolved in butanol. Examples of butanol used here are n-butanol, i-butanol, sec-butanol and tert-butanol, among which n-butanol is preferable. The amount of butanol is about 1 to 5 parts by weight, preferably about 2 to 3 parts by weight relative to 1 part by weight of the said soluble portion.

The mixed solution of the said soluble portion and butanol is stirred for about 0.5 to 1 hour at about 40 to 80° C., preferably at about 45 to 55° C. Next the mixture is slowly cooled to about 0 to 20° C., preferably about 3 to 10° C. over a period of usually about 2 to 5 hours. The cooled mixture is filtered through filter paper or filter fabric to recover a butanol-insoluble solid, and the filtrate containing a butanol-soluble impurity is discarded.

According to the method of the present invention, one or more solvents selected from the group consisting of water, methanol, ethanol and a mixture thereof is added, preferably while stirring, to the above cooled mixture. By adding these solvent(s), an insoluble solid is precipitated rapidly, by which operating efficiency can be improved. The amount of water to be added here is about 0.01 to 1 part by weight, preferably about 0.05 to 0.5 part by weight relative to 1 part by weight of the butanol used; the amount of methanol is about 0.01 to 5 parts by weight, preferably about 0.1 to 1 part by weight relative to 1 part by weight of the butanol used; and the amount of ethanol is about 0.01 to 10 parts by weight, preferably about 0.5 to 5 parts by weight relative to 1 part by weight of the butanol used. Although the temperature of solvent(s) to be added here may be ambient temperature, the same temperature as the cooled mixture, if possible, is preferable. The mixture consisting of mixed solvents is filtered through filter paper or filter fabric to recover a solid which is insoluble in the mixed solvent, and the filtrate containing a impurity which is soluble in the mixed solvent is discarded.

According to the method of the present invention, the butanol-insoluble or the mixed solvent-insoluble wherein butanol is a main component is washed with ethanol. The amount of ethanol is about 5 to 80 parts by weight, preferably about 10 to 40 parts by weight relative to 1 part by weight of the said insoluble. By washing with ethanol, butanol or the mixed solvent consisting mainly of butanol which is adhered to the surface of the said insoluble is eliminated, and consequently the removal of solvent in finishing process becomes easier.

A mixture of the said insoluble and ethanol is stirred for about 0.5 to 2 hour(s), preferably about 1 to 1.5 hour at ambient temperature. Next the mixture is filtered through filter paper or filter fabric to recover a lutein-fatty acid ester concentrate, and the filtrate containing an ethanol-soluble impurity is discarded.

Finally, the residual solvent is removed from the purified lutein-fatty acid ester concentrate by evaporation using, for example, a vacuum shelf dryer at a temperature of, for instance, lower than 50° C. preferably in the atmosphere of nitrogen gas.

The purity of lutein-fatty acid ester contained in the lutein-fatty acid ester concentrate which is obtained by the method according to the present invention is about not less than 70%, and that with about more than 80% purity is frequently obtained. As a result of this, the utilization range as a food color is broadened due to the vivid color tone, and it becomes possible to blend a lutein fatty-acid ester concentrate having high concentration into a dietary supplement by micro-encapsulation.

WORKING EXAMPLE

The following examples specifically illustrate the present invention.

A Method of Mesuring the Content of Lutein-Fatty Acid Ester

About 0.1 g of test sample was accurately measured and dissolved in hexane to make a 100 ml solution. It was diluted with hexane so that the resultant solution had absorbance ranging from 0.3 to 0.7, and then the maximum absorbance of the diluted solution around 445 nm was measured by a spectrophotometer. The content of lutein-fatty acid ester was calculated by the following formula.

Content(%)=((Absorbance÷Weight of Sample)×Dilution Ratio)÷1,394×100

Note: 1,394 is absorbance coefficient at 445 nm

Example 1

107 g of marigold oleoresin containing 26 wt % of lutein-fatty acid ester was mixed with 214 ml of acetone and dissolved at 50° C. under heating. Next the solution was slowly cooled to 20° C. over a period of about 3 hours and the resulting insoluble was eliminated by filtration, and then the filtrate was evaporated under reduced pressure to obtain a concentrate of the acetone-soluble portion. 300 g of n-butanol was added to this concentrate(100 g), and then the solution was dissolved at 45° C. under heating and slowly cooled to 4° C. over a period of about 4.5 hours.

After further keeping it at 4° C. for 16 hours, the resulting insoluble was filtered through filter paper. The solid which remained was mixed with 800 ml of ethanol, and the mixture was stirred, dispersed, washed at ambient temperature, and then filtered again through filter paper. The resulting solid was dried under vacuum to remove residual solvent, whereby 8.3 g of a concentrate containing 89 wt % of lutein-fatty acid ester was obtained.

Comparative Example 1

107 g of marigold oleoresin as used in Example 1 was mixed with 214 ml of acetone and dissolved at 50° C. under heating. The solution was slowly cooled to 20° C. over a period of about 3 hours and the resulting insoluble was eliminated by filtration, and then the filtrate was evaporated under reduced pressure to obtain a concentrate of acetone-soluble portion.

Next, according to the method mentioned in Example 1 of U.S. Pat. No. 6,191,298, this concentrate(100 g) was stirred for 3 hours with 200 g of isopropanol at ambient temperature to obtain a suspension. The suspension was filtered through filter paper and the solid left on the filter paper was dried under vacuum at ambient temperature to eliminate residual solvent, whereby 34.6 g of a solid containing 44 wt % of lutein-fatty acid ester was obtained.

Comparative Example 2

According to the method mentioned in Example 1 of U.S. Pat. No. 6,191,298, 100 g of marigold oleoresin as used in Example 1 was stirred for 3 hours with 200 g of isopropanol at ambient temperature to obtain a paste-like suspension. The suspension was filtered through filter paper and the solid left on the filter paper was dried under vacuum at ambient temperature to eliminate residual solvent, whereby 35.6 g of a concentrate containing 37 wt % of lutein-fatty acid ester was obtained.

Example 2

106 g of marigold oleoresin containing 22 wt % of lutein-fatty acid ester was mixed with 212 ml of acetone and dissolved at 50° C. under heating. Next the solution was slowly cooled to 20° C. over a period of about 3 hours and the resulting insoluble was eliminated by filtration, and then the filtrate was evaporated under reduced pressure to obtain a concentrate of acetone-soluble portion. 400 g of n-butanol was added to this concentrate(100 g), dissolved at 45° C. under heating, and slowly cooled to 4° C. over a period of about 4.5 hours.

26.3 g of water was added thereto and the resulting insoluble was filtered through filter paper. The solid obtained as above was mixed with 800 ml of ethanol for washing by stirring and dispersion at ambient temperature, and then filtered again through filter paper. The resulting solid was dried under vacuum to remove residual solvent, whereby 15.9 g of a concentrate containing 82 wt % of lutein-fatty acid ester was obtained.

Comparative Example 3 (No Acetone Treatment)

300 g of n-butanol was added to 100 g of marigold oleoresin as used in Example 2, dissolved at 45° C. under heating, and slowly cooled to 4° C. over about 4.5 hours. 32.6 g of water was added thereto and the resulting insoluble was filtered through filter paper. The solid obtained as above was mixed with 800 ml of ethanol for washing by stirring and dispersion at ambient temperature, and then filtered again through filter paper. The resulting solid was dried under vacuum to remove residual solvent, whereby 36.4 g of a concentrate containing 46 wt % of lutein-fatty acid ester was obtained.

Comparative Example 4 (No Butanol Treatment)

106 g of marigold oleoresin as used in Example 2 was mixed with 212 ml of acetone and dissolved at 50° C. under heating. Next the solution was slowly cooled to 20° C. over about 3 hours and the resulting insoluble was eliminated by filtration, and then the filtrate was evaporated under reduced pressure to obtain a concentrate of acetone-soluble portion. This concentrate (100 g) was mixed with 2,010 ml of ethanol for washing by stirring and dispersion at ambient temperature, and filtered again through filter paper. The resulting solid was dried under vacuum to remove the residual solvent, whereby 35.2 g of a concentrate containing 52 wt % of lutein-fatty acid ester was obtained.

Example 3

214 g of methanol was used in place of 26.3 g of water in Example 2, and 18.7 g of a concentrate containing 73 wt % of lutein-fatty acid ester was obtained.

Example 4

1,250 g of ethanol was used in place of 26.3 g of water in Example 2, and 18.4 g of a concentrate containing 77 wt % of lutein-fatty acid ester was obtained.

INDUSTRIAL APPLICABILITY

The method of the present invention provides a lutein-fatty acid ester concentrate of high purity, and as a result of this, the utilization range as a food color is broadened due to the vivid color tone of a lutein-fatty acid ester concentrate, and it becomes possible to blend a lutein-fatty acid ester concentrate having high concentration into a dietary supplement by micro-encapsulation.

What is claimed is:

1. A method for the production of a lutein-fatty acid ester concentrate of high purity from marigold oleoresin, which comprises:
    (a) a step of dissolving marigold oleoresin in a ketone solvent, cooling the solution and removing wherefrom a ketone solvent-insoluble impurity,
    (b) a step of dissolving a ketone solvent-soluble portion, obtained by removing a ketone solvent from the ketone solvent solution, in butanol, cooling the solution and eliminating a butanol-soluble impurity, and
    (c) a step of washing a butanol-insoluble, which is obtained after the above cooling process, with ethanol to eliminate an ethanol-soluble impurity, followed by removing a residual solvent to obtain a lutein-fatty acid ester concentrate of high purity.

2. A method for the production of a lutein-fatty acid ester concentrate of high purity from marigold oleoresin, which comprises:
    (a) a step of dissolving marigold oleoresin in a ketone solvent, cooling the solution and removing wherefrom a ketone solvent-insoluble impurity,
    (b) a step of dissolving a ketone solvent-soluble portion, which is obtained by removing a ketone solvent from the ketone solvent solution, in butanol, cooling the solution, and adding thereto one or more solvents selected from the group consisting of water, methanol, ethanol and a mixture thereof, and then eliminating a butanol-soluble impurity, and
    (c) a step of washing a butanol-insoluble, which is obtained upon addition of the said solvent(s) after cooling, with ethanol to eliminate an ethanol-soluble impurity, followed by removing a residual solvent to obtain a lutein-fatty acid ester concentrate of high purity.

3. A method for the production of a lutein-fatty acid ester concentrate of high purity, which comprises dissolving marigold oleoresin in a ketone solvent, cooling the solution and removing wherefrom a ketone solvent-insoluble impurity.

4. The method for the production of a lutein-fatty acid ester concentrate of high purity as claimed in claim 1, wherein the ketone solvent is acetone.

5. A method for the production of a lutein-fatty acid ester concentrate of high purity, which comprises washing a butanol-insoluble, which is precipitated from a butanol solution containing lutein-fatty acid ester obtained by processing marigold oleoresin, with ethanol.

6. The method for the production of a lutein-fatty acid ester concentrate of high purity as claimed in claim 1, wherein butanol is n-butanol.

7. The method for the production of a lutein-fatty acid ester concentrate of high purity as claimed in claim 2, wherein the ketone solvent is acetone.

8. The method for the production of a lutein-fatty acid ester concentrate of high purity as claimed in claim 3, wherein the ketone solvent is acetone.

9. The method for the production of a lutein-fatty acid ester concentrate of high purity as claimed in claim 2, wherein butanol is n-butanol.

10. The method for the production of a lutein-fatty acid ester concentrate of high purity as claimed in claim 5, wherein butanol is n-butanol.

* * * * *